(12) United States Patent
McDonnell et al.

(10) Patent No.: US 10,758,729 B2
(45) Date of Patent: Sep. 1, 2020

(54) INTERVENTIONAL MEDICAL SYSTEMS, CATHETERS, AND METHODS

(71) Applicant: Medtronic, Inc., Minneapolis, MN (US)

(72) Inventors: Paula McDonnell, Galway (IE);
Brendan P Geraghty, Galway (IE);
Gwenda Francis, Galway (IE); Rónán Wood, Galway (IE); Sean Ward, Dublin (IE); Pat McHugh, Ballyhaunis (IE); Tomas K Kelly, Galway (IE)

(73) Assignee: Medtronic, Inc., Minneapolis, MN (US)

( * ) Notice: Subject to any disclaimer, the term of this patent is extended or adjusted under 35 U.S.C. 154(b) by 1038 days.

(21) Appl. No.: 14/872,770

(22) Filed: Oct. 1, 2015

(65) Prior Publication Data

US 2017/0095662 A1   Apr. 6, 2017

(51) Int. Cl.
*A61N 1/362* (2006.01)
*A61N 1/375* (2006.01)
*A61N 1/05* (2006.01)
*A61N 1/372* (2006.01)

(52) U.S. Cl.
CPC .......... *A61N 1/362* (2013.01); *A61N 1/057* (2013.01); *A61N 1/0573* (2013.01); *A61N 1/3756* (2013.01); *A61N 1/37205* (2013.01); *A61N 2001/058* (2013.01); *A61N 2001/0578* (2013.01)

(58) Field of Classification Search
CPC ..... A61B 17/3468; A61B 90/11; A61N 1/362; A61N 2001/0578
See application file for complete search history.

(56) References Cited

U.S. PATENT DOCUMENTS 2,114,695 A   4/1938  Anderson
3,835,864 A   9/1974  Rasor et al.
4,655,219 A   4/1987  Petruzzi
(Continued)

OTHER PUBLICATIONS (PCT/US2016/061863) PCT Notification of Transmittal of the International Search Report and the Written Opinion of the International Searching Authority, dated Jan. 31, 2017, 11 pages.
(Continued)

*Primary Examiner* — George J Ulsh
(74) *Attorney, Agent, or Firm* — Shumaker & Sieffert, P.A.

(57) ABSTRACT

In a system for retrieving an implanted device, a flared inner surface of a catheter tubular sidewall may define a distal-most opening of a device receptacle; the opening has a first diameter equal to that of the receptacle, and a second diameter, coincident with a distal-most edge of the tubular sidewall, and at least 5% greater than the receptacle diameter. Alternately, a retrieval tool in sliding engagement within a lumen of a catheter includes a shaft assembly, through which a snare member passes, and which includes a collapsible spring-biased perimeter sidewall; the sidewall defines a capture member passageway approximately coaxial, and in fluid communication with a lumen of the shaft assembly. A distal-most opening of the passageway has a spring-biased diameter that is greater than that of a distal-most opening of a device receptacle of the catheter, and a collapsed diameter that is less than the receptacle distal-most opening diameter.

8 Claims, 14 Drawing Sheets

(56) References Cited

U.S. PATENT DOCUMENTS

| | | | |
|---|---|---|---|
| 4,710,181 A | 12/1987 | Fuqua | |
| 5,026,377 A | 6/1991 | Burton et al. | |
| 5,171,233 A | 12/1992 | Amplatz et al. | |
| 5,234,437 A | 8/1993 | Sepetka | |
| 5,350,397 A | 9/1994 | Palermo et al. | |
| 5,417,697 A * | 5/1995 | Wilk | A61B 18/10 606/113 |
| 5,476,510 A | 12/1995 | Eberhardt et al. | |
| 6,156,055 A * | 12/2000 | Ravenscroft | A61B 17/221 606/127 |
| 6,187,016 B1 | 2/2001 | Hedges et al. | |
| 6,277,125 B1 | 8/2001 | Barry et al. | |
| 6,348,056 B1 | 2/2002 | Bates et al. | |
| 6,355,060 B1 | 3/2002 | Lenker et al. | |
| 6,501,993 B2 | 12/2002 | Morgan et al. | |
| 6,506,205 B2 | 1/2003 | Goldberg et al. | |
| 6,846,317 B1 | 1/2005 | Nigon | |
| 6,953,473 B2 | 10/2005 | Porter | |
| 7,033,376 B2 | 4/2006 | Tsukernik | |
| 7,323,003 B2 | 1/2008 | Lowe | |
| 8,025,668 B2 * | 9/2011 | McCartney | A61B 8/0841 600/122 |
| 8,364,280 B2 | 1/2013 | Marnfeldt et al. | |
| 8,777,932 B2 | 7/2014 | Sage et al. | |
| 8,945,145 B2 * | 2/2015 | Tran | A61N 1/37205 606/129 |
| 9,237,948 B2 * | 1/2016 | Colson | A61F 2/243 |
| 9,480,850 B2 * | 11/2016 | Schmidt | A61N 1/3756 |
| 9,700,732 B2 * | 7/2017 | Schmidt | A61N 1/362 |
| 9,775,636 B2 * | 10/2017 | Fazio | A61B 17/320016 |
| 9,844,664 B2 * | 12/2017 | McEvoy | A61N 1/0573 |
| 2005/0159771 A1 * | 7/2005 | Petersen | A61F 2/01 606/200 |
| 2006/0085041 A1 | 4/2006 | Hastings et al. | |
| 2006/0247572 A1 * | 11/2006 | McCartney | A61B 8/0841 604/19 |
| 2007/0005131 A1 * | 1/2007 | Taylor | A61F 2/2433 623/2.11 |
| 2008/0065011 A1 * | 3/2008 | Marchand | A61F 2/2433 604/103.02 |
| 2009/0182370 A1 * | 7/2009 | Volobuyev | A61B 17/221 606/200 |
| 2012/0165827 A1 * | 6/2012 | Khairkhahan | A61N 1/362 606/129 |
| 2012/0172690 A1 | 7/2012 | Anderson et al. | |
| 2012/0172891 A1 * | 7/2012 | Lee | A61B 17/3468 606/129 |
| 2012/0184987 A1 * | 7/2012 | Sirota | A61F 2/01 606/200 |
| 2012/0239130 A1 | 9/2012 | Hartley et al. | |
| 2013/0053921 A1 * | 2/2013 | Bonner | A61N 1/3756 607/36 |
| 2013/0103047 A1 * | 4/2013 | Steingisser | A61N 1/3756 606/129 |
| 2013/0131591 A1 * | 5/2013 | Berthiaume | A61N 1/3756 604/95.04 |
| 2014/0142621 A1 | 5/2014 | Masters et al. | |
| 2014/0163579 A1 | 6/2014 | Tischendorf et al. | |
| 2015/0051609 A1 | 2/2015 | Schmidt et al. | |
| 2015/0051610 A1 * | 2/2015 | Schmidt | A61N 1/37205 606/129 |
| 2015/0051611 A1 * | 2/2015 | Schmidt | A61N 1/37205 606/129 |
| 2015/0094668 A1 * | 4/2015 | Wood | A61M 25/0105 604/256 |
| 2015/0094735 A1 * | 4/2015 | Ward | A61N 1/362 606/129 |
| 2015/0273212 A1 * | 10/2015 | Berthiaume | A61N 1/0587 600/424 |
| 2016/0015968 A1 * | 1/2016 | Bonner | A61N 1/0592 606/129 |
| 2016/0015983 A1 * | 1/2016 | Sheldon | A61N 1/371 606/129 |
| 2016/0143661 A1 * | 5/2016 | Wood | A61B 17/00234 606/129 |
| 2016/0243355 A1 * | 8/2016 | Wood | A61B 17/3468 |
| 2017/0028190 A1 * | 2/2017 | O'Carroll | A61N 1/05 |
| 2017/0100582 A1 * | 4/2017 | McEvoy | A61N 1/0573 |

OTHER PUBLICATIONS

Nova® Optional Accessories (1 page), accessed Nov. 16, 2015, http://www.panamericantool.com/9-32-40-aircraft-collets.html.
(PCT/US2016/038809) PCT Notification of Transmittal of the International Search Report and the Written Opinion of the International Searching Authority, dated Aug. 29, 2016, 10 pages.

* cited by examiner

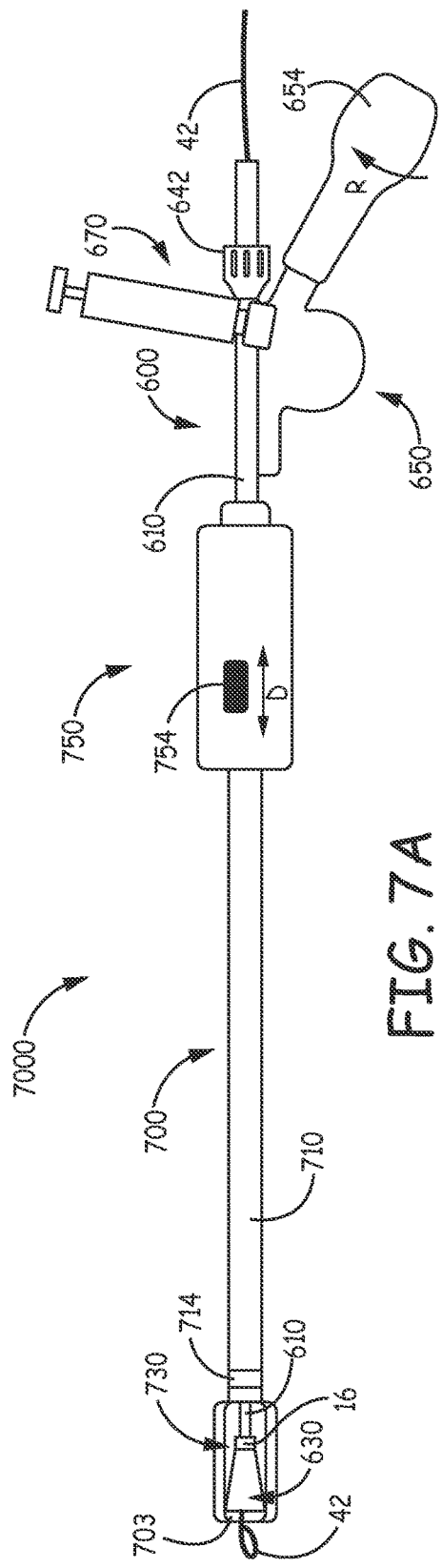
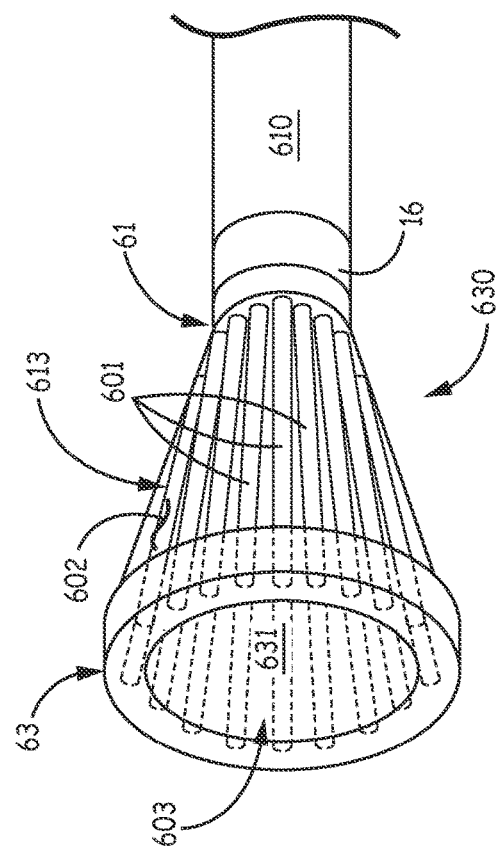
FIG. 7A
FIG. 7B

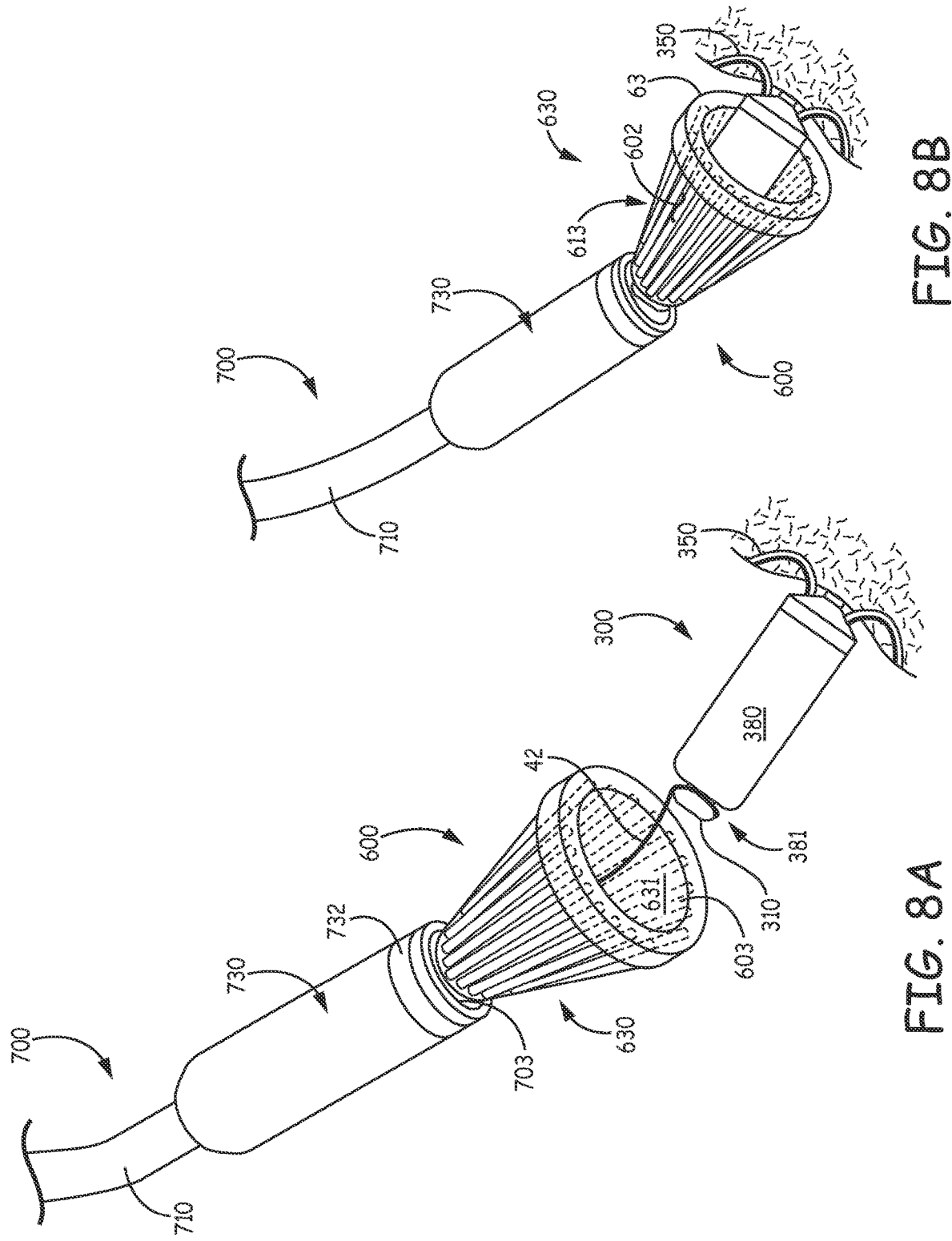

INTERVENTIONAL MEDICAL SYSTEMS, CATHETERS, AND METHODS

FIELD OF THE DISCLOSURE

The present disclosure pertains to interventional medical systems, and more particularly to systems, catheters and methods that are useful for retrieving medical devices from implant sites.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical and/or MRI compatibility issues, which are sometimes associated with elongate lead wires and well known to those skilled in the art, have motivated the development of implantable cardiac pacing devices that are wholly contained within a relatively compact package, the entirety of which is configured for implant in close proximity to the pacing site. FIG. 1 is a schematic diagram that shows potential cardiac implant sites for such a device, for example, within an appendage 102 of a right atrium RA, within a coronary vein CV (via a coronary sinus ostium CSOS), or in proximity to an apex 103 of a right ventricle RV, for example, as shown in FIG. 2.

FIG. 2 shows an implantable medical device 300 having been implanted by an operator using a catheter 200, for example, like the tool described in the commonly assigned United States Patent Application US 2015/0094668, wherein the operator advanced tool 200 into the right heart through the inferior vena cava IVC, for example, from a femoral vein access site, and then deployed device 300 from a device receptacle 230 of catheter 200. In some cases, when it may be necessary to retrieve the implanted device, the operator can employ catheter 200 to do so, but new and improved tools and methods would increase the ease and efficiency of retrieval.

SUMMARY

An interventional medical system, according to embodiments disclosed herein, includes features configured to accommodate misalignment between an implanted medical device and a distal-most opening of a device receptacle of a system catheter, when an operator employs the catheter to retrieve the device from the implant site.

In some embodiments, a tubular sidewall of the catheter, which defines the device receptacle, is improved to include a flared inner surface, wherein the inner surface defines the distal-most opening, so that the opening has a first diameter and a second diameter, the first diameter being equal to a diameter of the receptacle, and the second diameter, which is coincident with a distal-most edge of the tubular sidewall, being at least 5% greater than the diameter of the receptacle.

In alternate embodiments, a shaft assembly of a retrieval tool of the system includes a capture member formed by a collapsible spring-biased perimeter sidewall, wherein the perimeter sidewall defines a passageway approximately coaxial, and in fluid communication with a lumen formed by an elongate tubular sidewall of the retrieval tool shaft assembly. The retrieval tool lumen and passageway allow passage of a snare member of the retrieval tool therethrough, and the tool shaft assembly is configured for sliding engagement within the system catheter. A distal-most opening of the capture member passageway has a spring-biased diameter that is greater than a diameter of a distal-most opening of the device receptacle of the catheter, and has a collapsed diameter that is less than that of the device receptacle, when the capture member is received within therein.

In some embodiments, the collapsible spring-biased perimeter sidewall of the aforementioned capture member includes a flexible polymer mesh supported by a plurality of spring-biased ribs, and the system may further include a vacuum source configured for applying suction through the lumen and capture member passageway of the retrieval tool shaft assembly. The spring biased diameter of the distal-most opening of the capture member passageway in these embodiments may be 2 to 5 times greater than the diameter of the device receptacle distal-most opening. In some alternate embodiments, the elongate tubular sidewall of the retrieval tool shaft assembly includes a flared distal end, and the collapsible spring-biased perimeter sidewall of the capture member includes a 'serpentined' wire loop mounted to the flared distal end. The spring biased diameter of the distal-most opening of the capture member passageway in these alternate embodiments is at least 5% greater than the diameter of the device receptacle distal-most opening.

According to some embodiments, an inner assembly of a catheter is formed by a shaft subassembly that includes the elongate tubular member with the flared distal end and the 'serpentined' wire loop of the capture member mounted thereto. And, according to some methods, the catheter may be converted from a deployment configuration, in which a device tether extends through lumens of the tubular member, to a retrieval configuration, by removing the device tether from the lumens and then inserting capture member tethers into the lumens, to couple the collapsible spring-biased perimeter sidewall of the capture member to the tubular sidewall.

According to some additional methods disclosed herein, an operator may employ any of the above-described retrieval tools in retrieving the medical device from an implant site, for example, according to the following steps. The operator first advances the device receptacle of the catheter to the implant site, so that the distal-most opening of the device receptacle is located in proximity to the device, and then either advances the retrieval tool out through the distal-most opening of the device receptacle of the catheter, in some embodiments, or retracts the device receptacle to expose the capture member, in some alternate embodiments, so that the spring-biased sidewall of the capture member of the tool opens to the spring-biased diameter. Then, the operator may maneuver the retrieval tool to snare an attachment feature of the device. Once the device attachment feature is snared, the operator advances the capture member of the retrieval tool over the snared device attachment feature and a proximal end of the device housing, to which the attachment feature is joined, after which, the operator may apply a pull force, to disengage the device fixation member from the implant site. In some cases, the operator advances the capture member of the retrieval tool over the snared device until a distal edge of the spring-biased sidewall thereof abuts the implant site, and then applies suction through the capture member passageway while applying the pull force.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 7A is a plan view, with a partial cross-section view, of an interventional medical system, according to some alternate embodiments;

FIG. 7B is an enlarged perspective view of a portion of the system, according to some embodiments;

FIGS. 8A-B are schematics outlining some methods of use corresponding to the system of FIGS. 7A-B;

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 3:
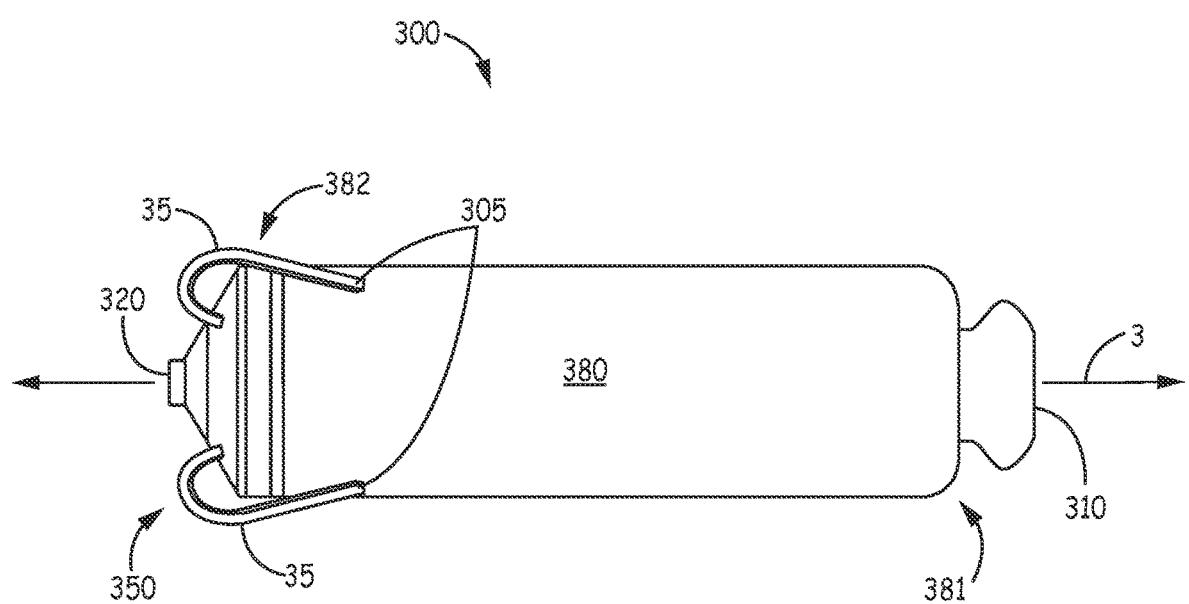
FIG. 3 is a plan view of the exemplary relatively compact implantable medical device, which may be part of an interventional medical system, according to some embodiments.

FIG. 3 is a plan view of exemplary relatively compact implantable medical device 300, which may be part of an interventional medical system, for example, according to some embodiments described below. FIG. 3 illustrates device 300 including a hermetically sealed housing 380 extending from a proximal end 381 thereof to a distal end 382 thereof and along a longitudinal axis 3. Device 300 further includes an electrode 320 and a fixation member 350, both mounted in proximity to distal end 382 of housing 380, and an electronic controller (not shown), for example, a pulse generator and an associated power supply, contained in housing 380, wherein electrode 320 is electrically coupled to the controller via a hermetically sealed feedthrough assembly (not shown) such as is known in the art. Housing 380, for example, formed from a biocompatible and biostable metal such as titanium, may be overlaid with an insulative layer, for example, medical grade polyurethane, parylene, or silicone, and, although not shown, device 300 may include another electrode, for example, formed by removing a portion of the insulative layer to expose the metallic surface of housing 380. The other electrode may function in conjunction with electrode 320 for bipolar pacing and sensing, when fixation member 350 secures electrode 320 in intimate tissue contact at a target implant site. FIG. 3 further illustrates device 300 including an attachment feature 310 joined to proximal end 381 of housing 380, wherein feature 310 is configured for snaring, for example, by an elongate snare member 42, which is described below in conjunction with FIG. 4A.

With further reference to FIG. 3, device fixation member 350 includes a plurality of fingers 35 spaced apart from one another around a perimeter of device housing distal end 382. Although only two fingers 35 of fixation member 350 are shown in FIG. 3, fixation member 350 may include as many as eight fingers 35. According to an exemplary embodiment, fixation fingers 35 are integrally formed with one another, having been cut from Nitinol tubing, according to methods known in the art. After cutting the Nitinol tubing, fingers 35 may be shaped by bending and holding fingers 35 in the illustrated curvature while heat treating, according to methods known to those skilled in the art. Fixation member 350 may be mounted to distal end 382 of device housing 380, for example, in a manner similar to that described for a fixation component 102 in co-pending and commonly assigned United States Patent Application 2012/0172690, which description is hereby incorporated by reference. The superelastic nature of Nitinol allows fingers 35 to elastically deform between a relaxed condition, which is shown, and an extended condition, in which a free end 305 of each finger extends distally away from distal end 382 of device housing 380, for example, as shown in FIGS. 6B and 10B.

Figure 2:
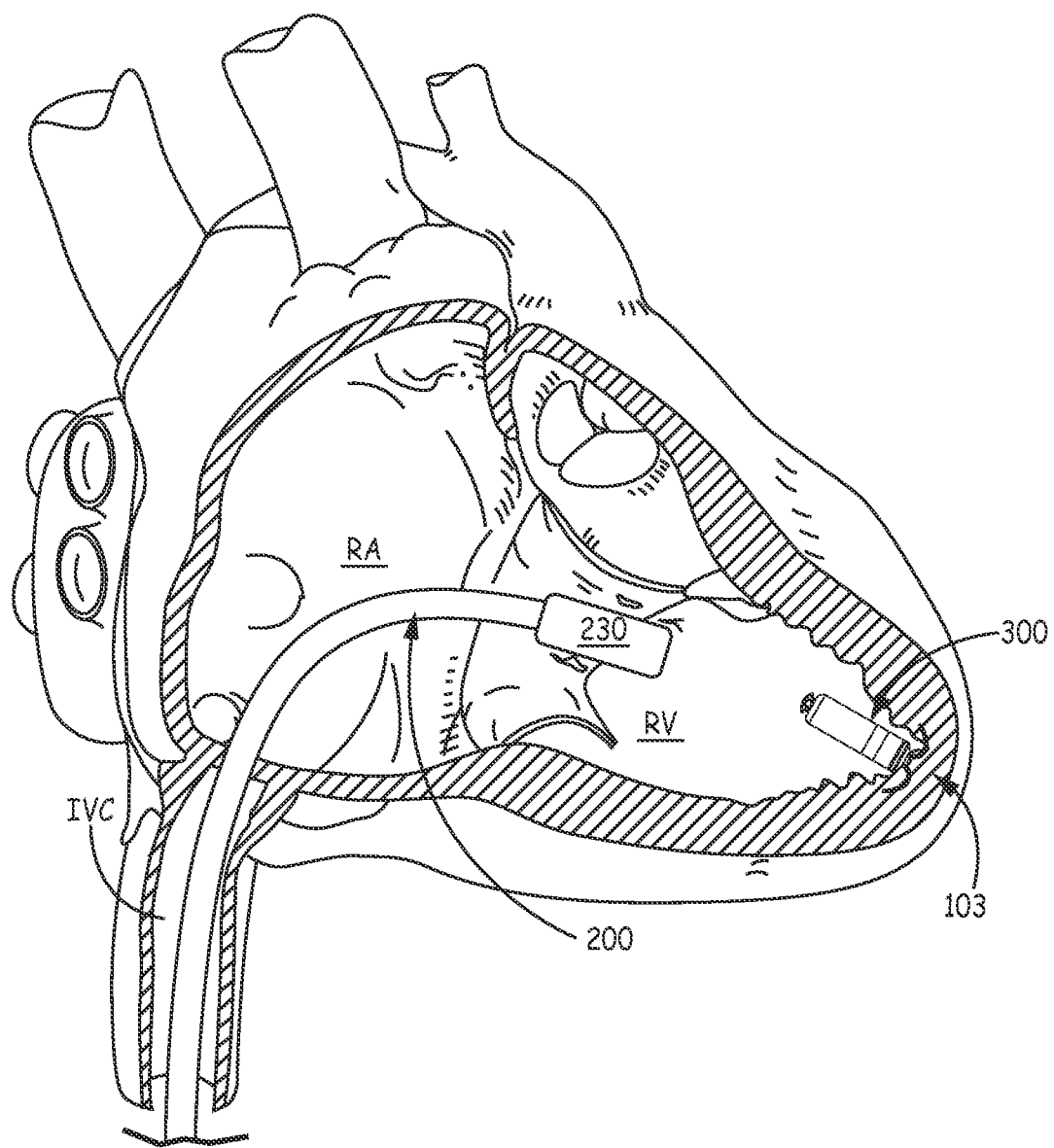
FIG. 2 is a schematic showing an exemplary relatively compact implantable medical device having been delivered from a catheter to an implant site.
Figure 4A:
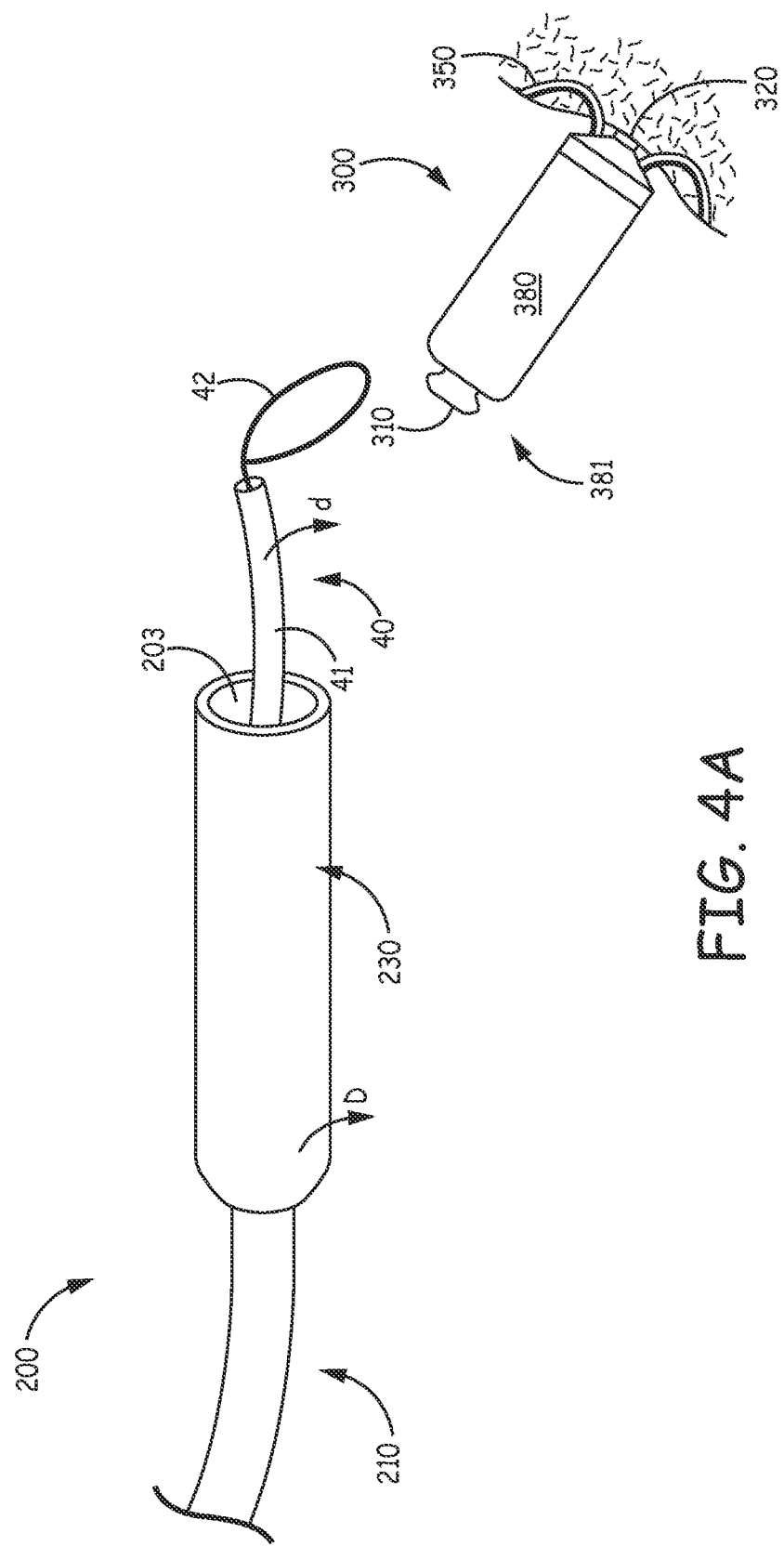
FIGS. 4A-B are schematics depicting a difficulty in retrieving an implanted medical device.
Figure 4B:
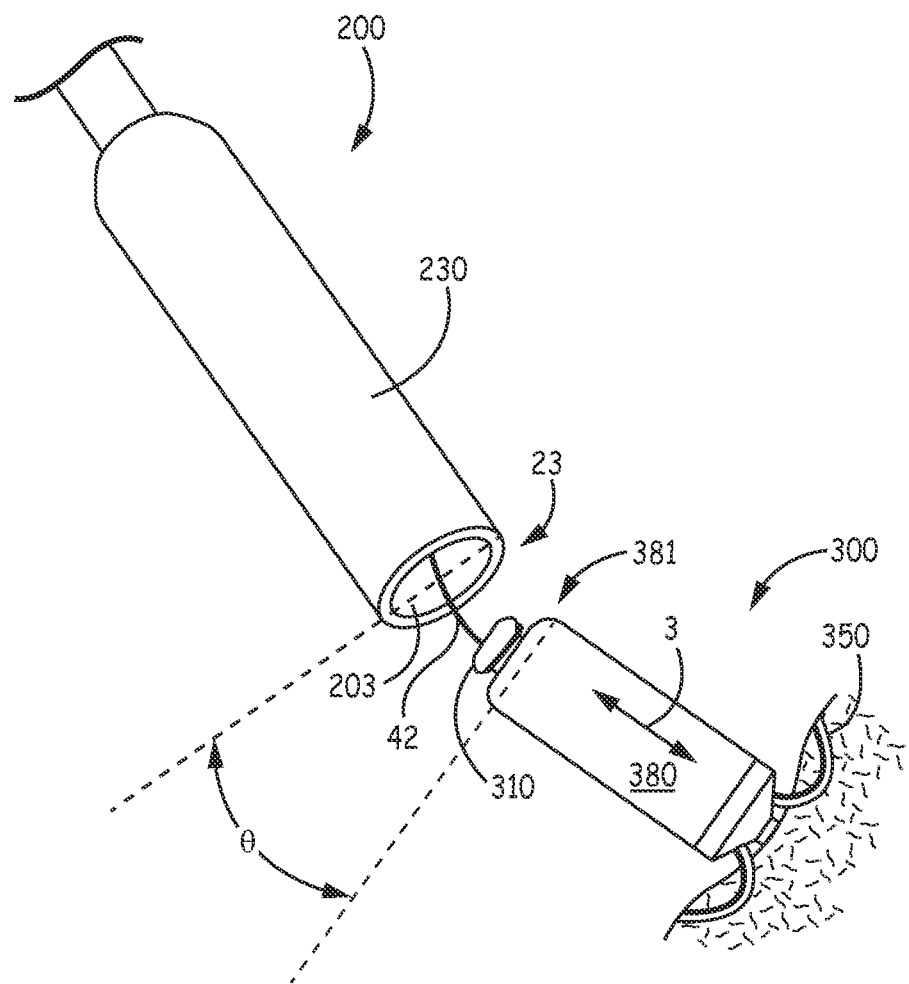

FIGS. 4A-B are schematics depicting a difficulty that may be encountered by an operator when attempting to retrieve medical device 300 from an implant site, for example, the site in proximity to an apex 103 of a right ventricle RV shown in FIG. 2. FIG. 4A illustrates device receptacle 230 of catheter 200 having been advanced to the implant site, and a device retrieval tool 40 having been passed out through a distal-most opening 203 of receptacle 230. Retrieval tool 40 includes elongate snare member 42, which extends within a shaft 41 of tool 40, wherein snare member 42 may be a medical grade Nitinol wire that has a diameter of between approximately 0.020 inch and approximately 0.040 inch, and is slideably engaged within shaft 41 to open and close a loop thereof. Snare member 42 is shown deployed to snare device attachment feature 310, and the operator may deflect, per arrow d, shaft 41, via a steering assembly thereof, to maneuver the deployed snare member 42 into position around attachment feature 310. (FIG. 5A illustrates a pull band 14 mounted to shaft 41 of tool 40, and an actuator 454 mounted to a handle 45 of tool 40, both of the steering assembly, wherein those skilled in the art will understand that an elongate pull wire extends within shaft 41 and has a distal end coupled to pull band 14 and a proximal end coupled to actuator 454.)

Figure 1:
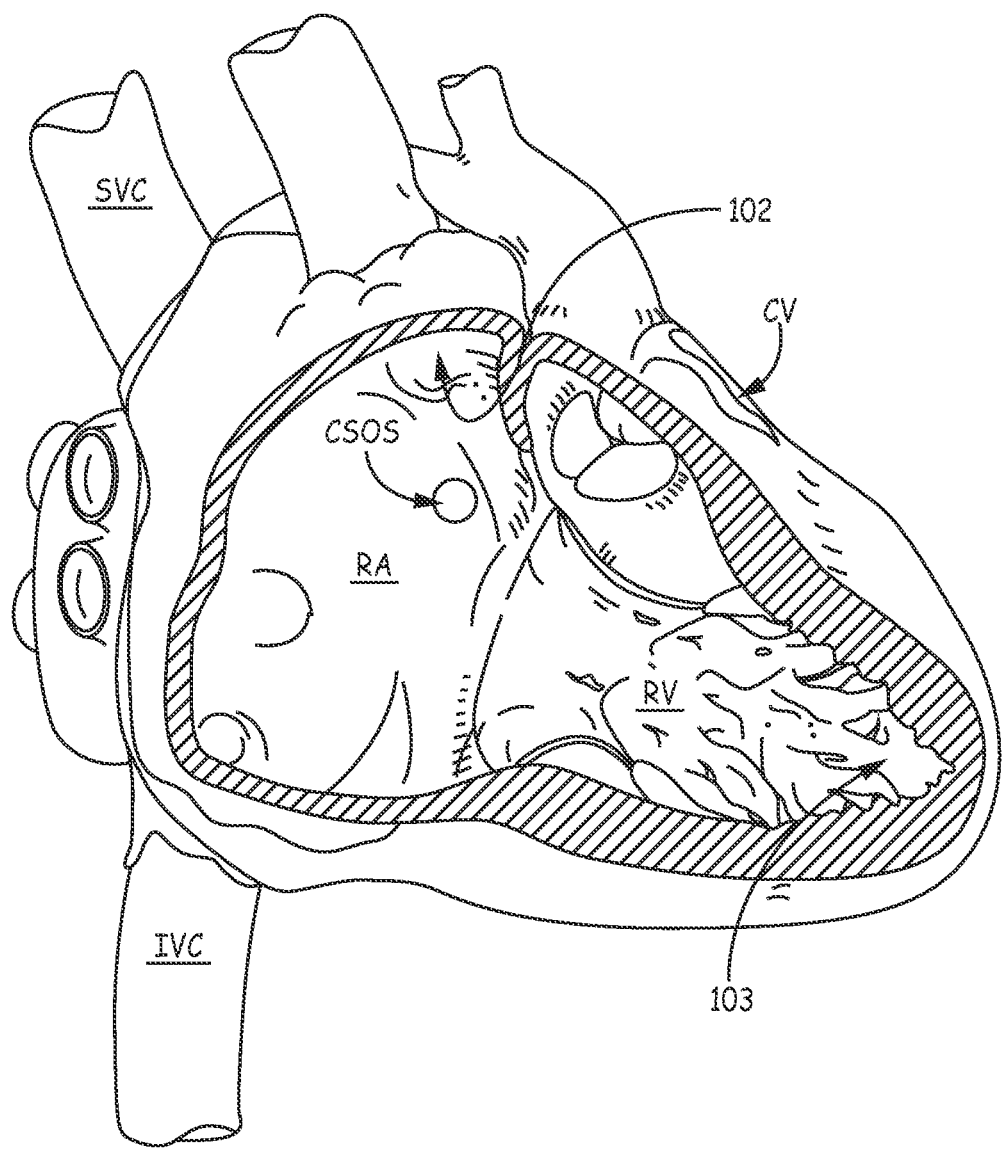
FIG. 1 is a schematic diagram showing potential implant sites for a relatively compact implantable medical device.

Once the operator has snared attachment feature 310, the operator may advance catheter 200 over retrieval tool 40 until opening 203 is brought into proximity with device housing proximal end 381, as shown in FIG. 4B. FIG. 4B illustrates an angle θ that corresponds to a misalignment of a plane of distal-most opening 203 of receptacle 230 and a plane of proximal end 381 (approximately orthogonal to longitudinal axis 3 of device 300). The misalignment will likely cause a distal-most edge 23 of receptacle 230 to catch on an edge of device proximal end 381, so that the operator may find it difficult to advance receptacle 230 over the snared device 300, or to pull the snared device 300 into receptacle 230. The angle of misalignment θ encountered in some cardiac implant sites, for example, in appendage 102 of the right atrium RA, or near apex 103 of the right ventricle RV (FIG. 1), may be as great as 45 degrees.

Figure 5A:
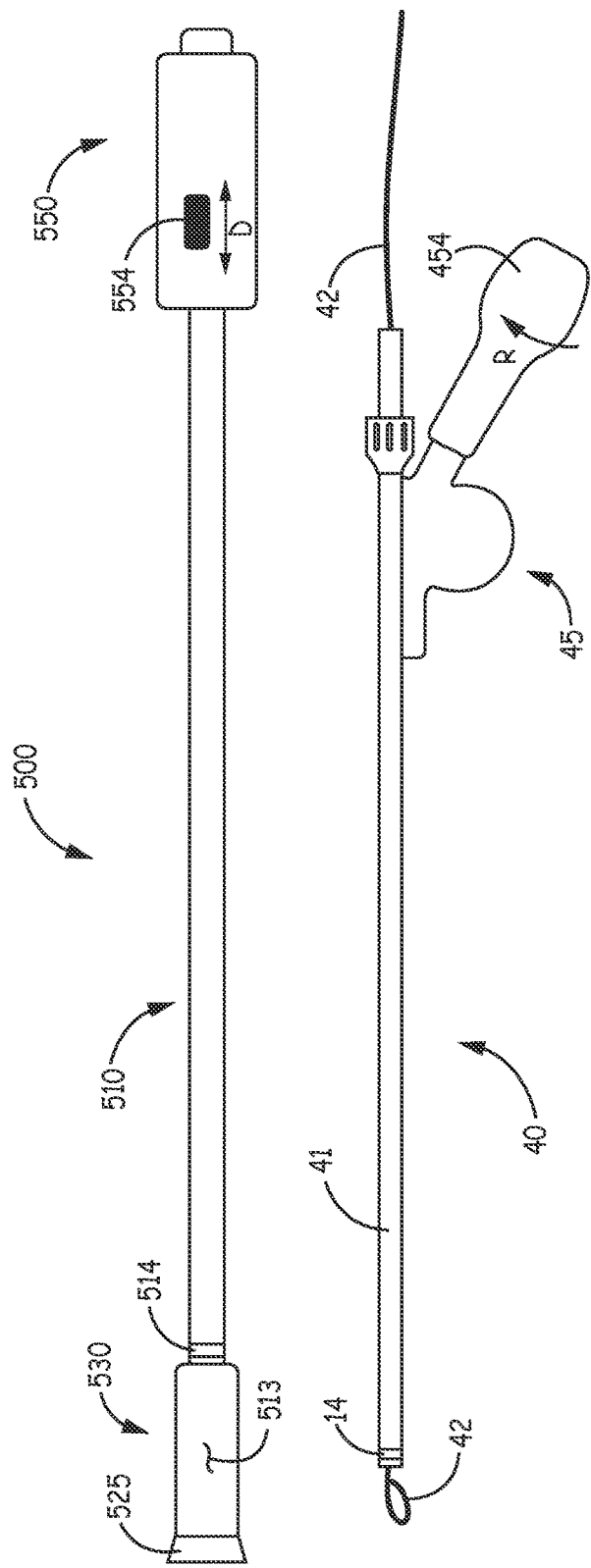
FIG. 5A is a plan view of a catheter and an associated retrieval tool of an interventional medical system, according to some embodiments.
Figure 5B:
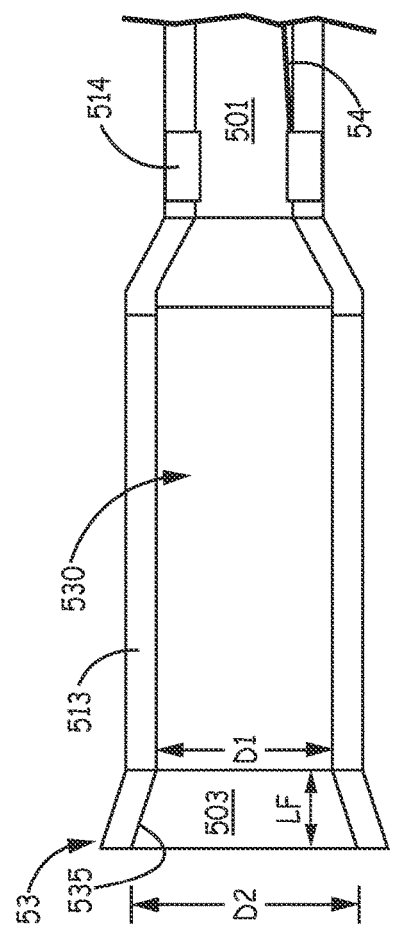
FIG. 5B is a longitudinal cross-section view of a portion of the catheter, according to some embodiments.

FIG. 5A is a plan view of a catheter 500 and retrieval tool 40, which may be included in an interventional medical system, according to some embodiments; and FIG. 5B is a longitudinal cross-section view of a distal portion of catheter 500, according to some embodiments. FIG. 5A illustrates catheter 500 including an elongate shaft 510, a handle 550 joined to a proximal end of shaft 510, and a tubular sidewall 513 joined to a distal end of shaft 510, wherein tubular sidewall 513 defines a device receptacle 530. With reference to FIG. 5B, shaft 510 includes a longitudinally extending lumen 501 configured to receive passage of device retrieval tool 40 therethrough, wherein device receptacle 530 is in fluid communication with lumen 501. Lumen 501 may have a diameter of approximately 0.154 inch (3.9 mm). Catheter 500 and retrieval tool 40 may be employed together to retrieve medical device 300 from an implant site, for example, as described above in conjunction with FIGS. 4A-B. But, according to the illustrated embodiment, tubular sidewall 513 is improved to include a flared inner surface 535 that defines a distal-most opening 503 of receptacle 530, and thereby alleviates the above-described difficulty associated with angle of misalignment θ, for example, as shown in the schematic of FIG. 6A.

With further reference to FIG. 5B, distal-most opening has a first diameter D1, which corresponds to that of receptacle 530, and a second diameter D2, which is coincident with a distal-most edge 53 of tubular sidewall 513. Second diameter D2 may be at least 5% greater than first diameter D1, or up to approximately 25% greater than first diameter D1 in some embodiments, wherein a length LF of flared inner surface 535 may be between 0.003 inch and 0.005 inch. The portion of sidewall 513 along length LF may also function as a radiopaque marker, for example, being formed from a medical grade polyamide material with a radiopaque filler, for example, Tungsten-filled Vestamid®, that is bonded to the remainder of sidewall 513, which may be formed from a medical grade polyether block amide (e.g., PEBAX® 7233 SA-01). A thickness of sidewall 513 may be approximately 0.004 inch along length LF, whereas a wall thickness along a length LR of receptacle 530 may be approximately 0.006 inch. According to the illustrated embodiment, the diameter of receptacle 530, which is equal to D1, is uniform along length LR thereof, and is sized to hold fingers 35 of device fixation member 350 in the extended condition, with free ends 305 thereof supported by diameter D1, when device 300 is contained therein, for example, as shown in FIG. 6B. In an exemplary embodiment, diameter D1 is approximately 0.3 inch (7.6 mm), and length LR is at least 31 millimeters.

Catheter shaft 510, for example, extending over a length of approximately 100 cm, may be formed by a stainless steel braid-reinforced medical grade polymer, for example, one or more appropriate grades of polyether block amide, which are arranged for decreasing stiffness from handle 550 to shaft distal end (e.g., PEBAX® 3533, 6333, 4033, and 7233). In some preferred embodiments, catheter 500 further includes a steering assembly, which is similar to that described above for tool 40. FIGS. 5A-B illustrate the steering assembly including a pull band 514, which is mounted to shaft 510 in proximity to the distal end thereof, an actuator 554, which is mounted to handle 550, and an elongate pull wire 54, which extends along a length of shaft 510, and which has a distal end coupled to pull band 514 and a proximal end coupled to actuator 554, so that moving actuator 554 per arrow D causes pull wire 54 to deflect the distal end of shaft 510. Although not shown, catheter shaft 510 may include a pre-formed curvature in proximity to receptacle 530.

Figure 6A:
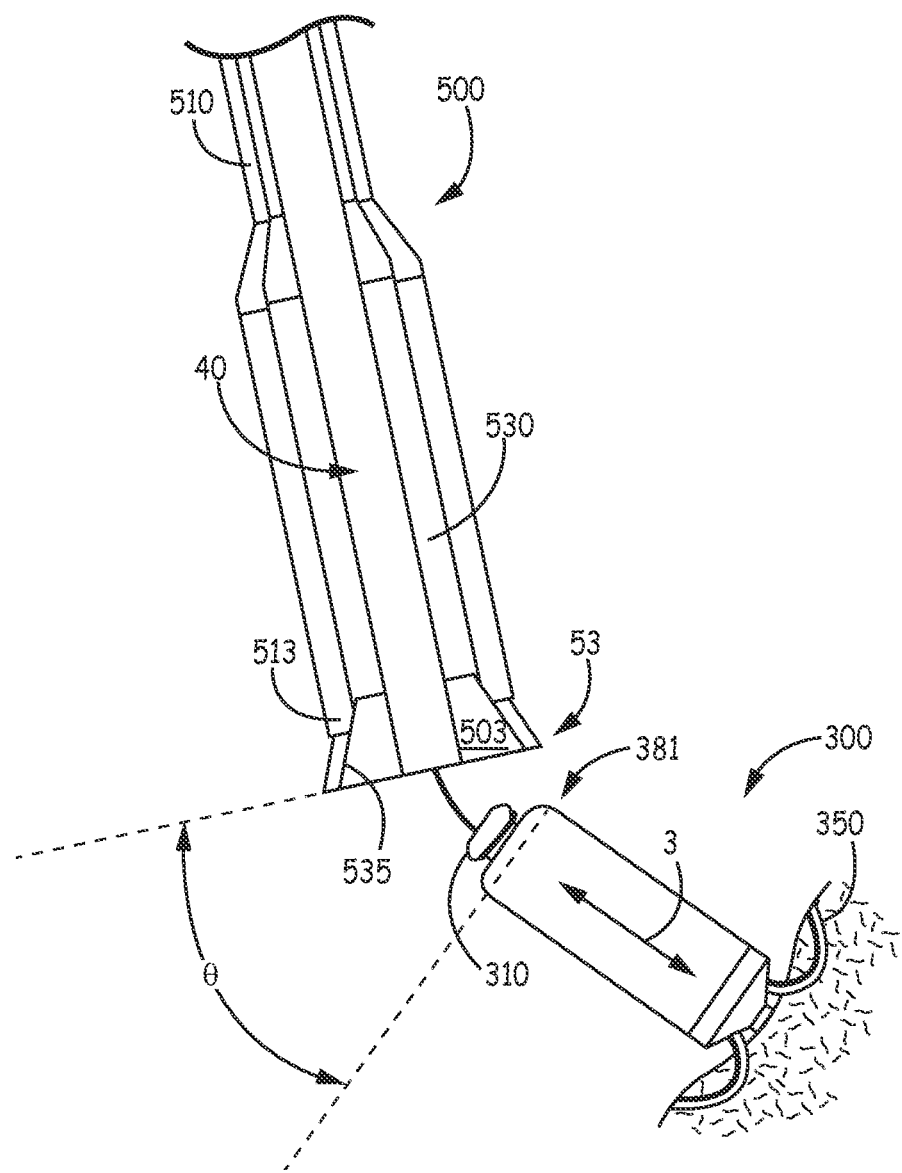
FIG. 6A is a schematic depicting the employment of the system of FIGS. 5A-B, according to some methods.
Figure 6B:
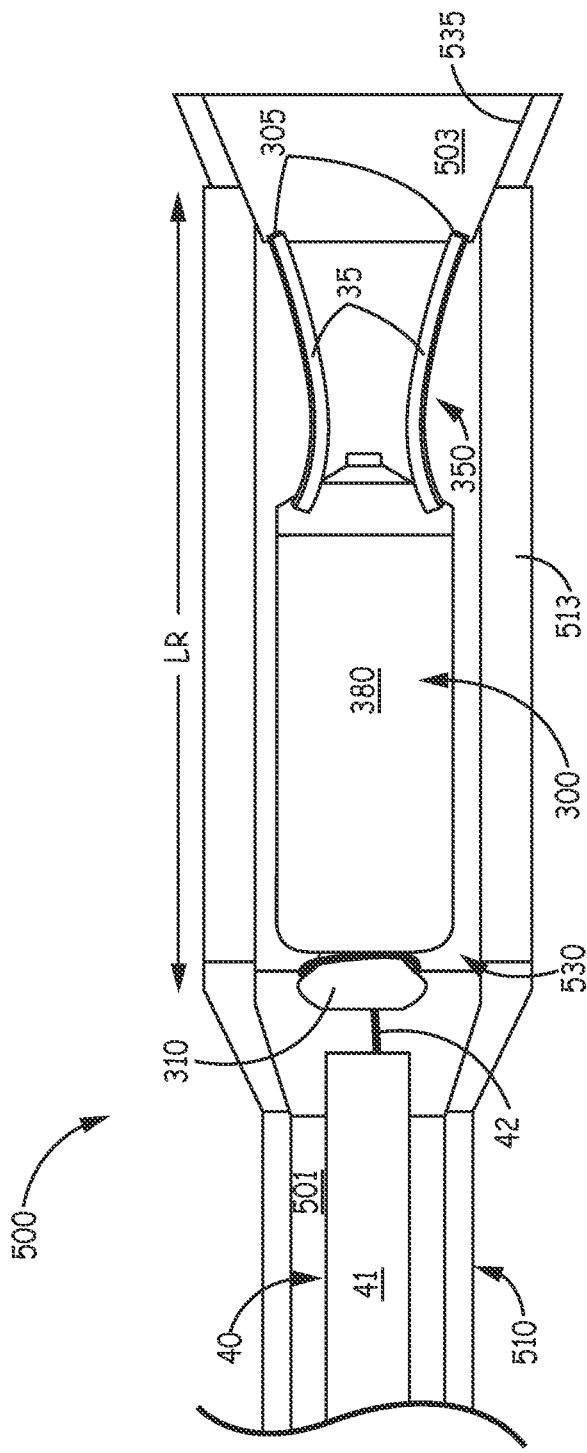
FIG. 6B is a longitudinal cross-section view of the system of FIGS. 5A-B, according to some embodiments.

FIG. 6A illustrates retrieval tool 40 having been passed through the positioned catheter 500 and manipulated to snare attachment feature 310 of the implanted device 300 device. Like the situation described above in conjunction with FIG. 4B, the plane of receptacle distal-most opening 503 is misaligned with that of device proximal end 381, by angle θ. But, due to flared inner surface 535, which defines distal-most opening 503, receptacle 530 can be "funneled" over the snared device 300, after which, the operator may apply a pull force to retrieval tool 40 to disengage device fixation member 350 from the implant site and bring device fixation member 350 into receptacle 530, so that fingers 35 thereof are held in the extended condition, as illustrated in FIG. 6B.

FIG. 7A is a plan view, with a partial cross-section view, of an interventional medical system 7000, according to some alternate embodiments. FIG. 7A illustrates system 7000 including a catheter 700 and a retrieval tool 600, which is in sliding engagement within a lumen (not shown) of an elongate shaft 710 of catheter 700. The partial cross-section view shows the above described elongate snare member 42 of tool 600 and a portion of a shaft assembly of tool 600 extending within a device receptacle 730 of catheter 700, which is joined to a distal end of shaft 710. Device receptacle 730, in some exemplary embodiments, may be formed from a medical grade polyether block amide (e.g., PEBAX® 7233 SA-01), while shaft 710 for example, extending over a length of approximately 100 cm, may be formed by a stainless steel braid-reinforced medical grade polymer, for example, one or more appropriate grades of polyether block amide, which are arranged for decreasing stiffness from a handle 750 of catheter 700 to shaft distal end (e.g., PEBAX® 3533, 6333, 4033, and 7233).

According to the illustrated embodiment, the shaft assembly of retrieval tool 600 includes an elongate tubular sidewall 610 and a capture member 630 joined thereto. Tubular sidewall 610 is configured for sliding engagement within the lumen of catheter shaft 710, and tubular sidewall 610 defines a lumen (not shown) in fluid communication with a passageway 631 of capture member 630 (FIG. 7B). The lumen of tubular sidewall 610 and capture member passageway 631 receive snare member 42 in sliding engagement, so that snare member 42 may be advanced out through capture member passageway 631, in order to retrieve a device, such as device 300, from an implant site, for example, as shown in FIG. 8A.

FIG. 7B is an enlarged perspective view of capture member 630, according to some embodiments, when capture member 630 is not constrained by device receptacle 730 of catheter 700, for example, having been advanced out through a distal-most opening 703 of receptacle 730. FIG. 7B illustrates capture member 630 including a collapsible spring-biased perimeter sidewall 613 that defines passageway 631, wherein passageway 631 is approximately coaxial, and in fluid communication with the lumen of tubular sidewall 610 of the retrieval tool shaft assembly. Perimeter sidewall 613 is shown extending from a proximal end thereof 61 to a distal end thereof 63, wherein proximal end 61 is coupled to tubular sidewall 610, and distal end 63 defines a distal-most opening 603 of passageway 631. FIG. 7A shows perimeter sidewall 613 of capture member 630 constrained within device receptacle 730 of catheter 700 so that distal-most opening 603 is at a collapsed diameter, while FIG. 7B shows distal-most opening 603 of capture member passageway 631 at a spring-biased diameter that is 2-5 times greater than a diameter of distal-most opening 703 of device receptacle 730. In either instance, capture member passageway 631 is sized to contain at least attachment member 310 and housing proximal end 381 of device 300. According to some exemplary embodiments, perimeter sidewall 613 includes a flexible polymer mesh 602 supported by a plurality of spring-biased ribs 601, for example, a weave of medical grade polyester fibers supported by Nitinol wires, wherein a proximal end of each rib 601 defines proximal end 61 of perimeter sidewall 613, and the rib proximal ends are spaced apart from one another around a circumference of tubular sidewall 610 of the retrieval tool shaft assembly. Polymer mesh 602 may be sown in place, and/or bonded, at either end of ribs 601, according to methods known to those skilled in the art. According to the illustrated embodiment, collapsible spring-biased perimeter sidewall 613 defines a flared outer surface of capture member 630, and in some preferred embodiments, a length of capture member passageway 631 is approximately equal to an overall length of medical device 300 so that fingers 35 of device fixation member 350 can be held inside passageway 631, when fixation member 350 is disengaged from the implant site in retrieving device 300.

FIGS. 8A-B are schematics outlining some methods of use corresponding to system 7000. FIG. 8A illustrates retrieval tool 600, having been passed through distal-most opening 703 of catheter 700, wherein device receptacle 730 of catheter 700 may be positioned in proximity to an implant site near apex 103 of a right ventricle RV shown in FIG. 2, for example, having been advanced through a 23 F introducer sheath that provides vascular access at a femoral vein puncture site (not shown). Device receptacle 730 is shown including a radiopaque marker band 732, which is located in proximity to distal-most opening, according to some preferred embodiments, wherein marker band 732 may be formed a Tungsten filled polymer, for example, 75% Tungsten and 25% Vestamid® L2140, which is heat bonded to receptacle 730, for example, while being secured thereto with a sacrificial heat-shrink tube. FIG. 8A further illustrates tool 600 having been maneuvered to snare attachment feature 310 of the implanted device 300. With reference back to FIGS. 7A-B, retrieval tool 600 further includes a steering assembly similar to that described above for retrieval tool 40. For example, FIG. 7A illustrates an actuator 654 of the steering assembly mounted to a handle 650 of tool 600, which is coupled to a proximal end of tubular sidewall 610, and FIGS. 7A-B further illustrate a pull band 16 mounted to tubular sidewall 610 in proximity to the distal end thereof, wherein a pull wire (not shown), which extends within tubular sidewall 610, has a proximal end coupled to actuator 654, and a distal end coupled to pull band 16. Thus, the operator can deflect the shaft assembly via the steering assembly, while maneuvering retrieval tool 600, by rotating actuator 654, for example, per arrow R. With further reference to FIG. 7A, catheter 700 may also include a similar steering assembly in some embodiments, wherein a pull band 714 is mounted in proximity to the distal end of catheter shaft 710, and an actuator 754 is mounted to handle 750 of catheter 700, being movable, per arrow D, to deflect the distal end of shaft 710 via a pull wire (not shown) that extends along shaft 710 with a proximal end coupled to actuator 754 and a distal end coupled to pull band 714, for example, as described above for catheter 500 of FIG. 5A.

With further reference to FIG. 8A, similar to the situations described above in conjunction with FIGS. 4B and 6A, the plane of receptacle distal-most opening 703 is misaligned with that of device proximal end 381. But, due to the expanded distal-most opening 603 of capture member passageway 631, at the spring-biased diameter, the operator can 'funnel' attachment feature 310 and proximal end 381 of device housing 380 into passageway 631, after which the operator can more easily advance receptacle 730 over the snared device 300. With reference to FIG. 8B, according to some embodiments and methods, the operator may advance capture member 630 over the snared device 300 until distal end 63 of spring-biased sidewall 613 abuts the implant site, and then apply a suction force through the lumen of the retrieval tool shaft assembly while applying a pull force to disengage device fixation member 350 from the implant site. The suction may draw any emboli, for example, released during the disengagement of device 300 from the implant site, into polymer mesh 602 of capture member spring biased perimeter sidewall 613, for containment within catheter 700 when the operator subsequently advances catheter 700 over retrieval tool 600, to bring device 300 and capture member 630 into device receptacle 730, according to some methods. With reference back to FIG. 7A, system 7000 is shown including an optional vacuum source 670 in the form of a syringe, which is coupled to handle 650 of retrieval tool 600 for fluid communication with the lumen defined by tubular sidewall 610. FIG. 7A further illustrates a proximal sealing member 642 of handle 650, for example, a Touhy Borst type, through which snare member 42 passes, and which provides an adequate seal for vacuum source 670 to apply suction in capture member passageway 631.

Figure 9A:
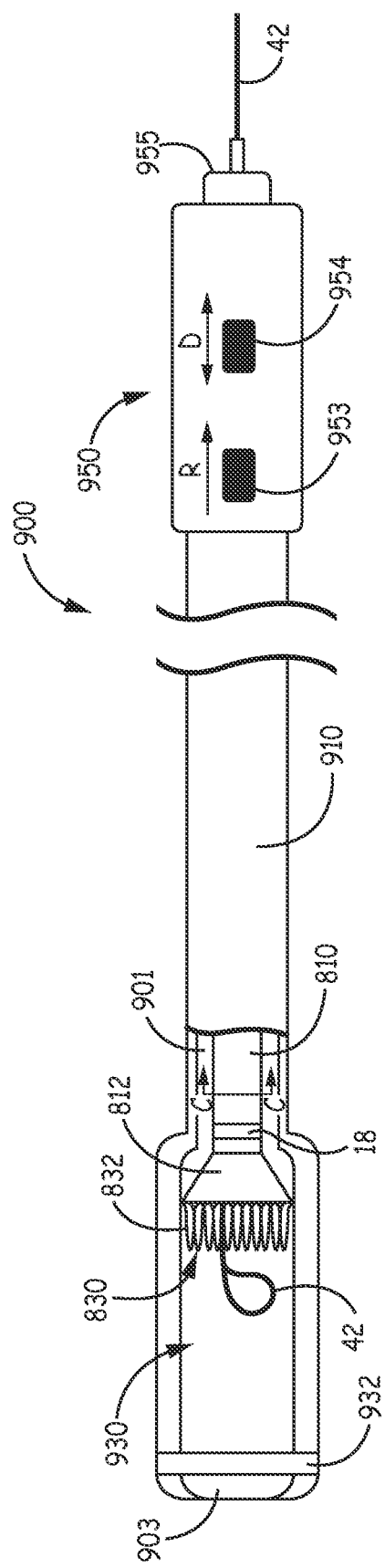
FIG. 9A is a plan view, with a partial cross-section view, of a catheter of an interventional medical system, according to yet further embodiments.

FIG. 9A is a plan view, with a partial cross-section view, of a catheter 900 of an interventional medical system, according to yet further embodiments, which has a retrieval tool integrated together therewith, for example, as an inner assembly extending within an outer assembly of catheter 900. It should be noted that, according to some alternate embodiments, the retrieval tool of catheter 900, rather than being an inner assembly of catheter 900, as described below, may be separate from catheter 900 and include a handle like tool 600 of system 7000. FIG. 9A illustrates the outer assembly of catheter 900 including a shaft 910 and a receptacle 930 that is coupled to a distal end of shaft 910 and in fluid communication with a longitudinally extending lumen 901 of shaft 910. Catheter shaft 910, for example, extending over a length of approximately 100 cm, may be formed by a stainless steel braid-reinforced medical grade polymer, for example, one or more appropriate grades of polyether block amide, which are arranged for decreasing stiffness from a handle 950 of catheter 900 to shaft distal end (e.g., PEBAX® 3533, 6333, 4033, and 7233). Although not shown, catheter shaft 910 may include a pre-formed curvature in proximity to receptacle 930. Device receptacle 930, in some exemplary embodiments, may be formed from a medical grade polyether block amide (e.g., PEBAX® 7233 SA-01), and preferably includes a radiopaque marker band 932 integrated therein. According to some embodiments, marker band 932 is formed from a Tungsten filled polymer, for example, 75% Tungsten and 25% Vestamid® L2140, which is heat bonded to receptacle 930, for example, while being secured thereto with a sacrificial heat-shrink tube. According to some alternate embodiments, marker band 932 is a gold foil, for example, having a thickness of approximately ten microns, which is secured around receptacle 930 by a reflow of the material thereof thereover. In yet further embodiments, a radiopaque filler, such as Tungsten, may be blended with the aforementioned PEBAX® material prior to extruding receptacle 930. A diameter of receptacle 930, is sized to hold fingers 35 of device fixation member 350 in the extended condition, with free ends 305 thereof supported, when device 300 is contained therein, for example, as shown in FIG. 10B. In an exemplary embodiment, the diameter of receptacle 930 is approximately 0.3 inch (7.6 mm), and a length thereof is at least 31 millimeters. FIG. 9A further illustrates a control member 953 of handle 950, which is coupled to shaft 910 for retraction thereof, per arrow R, relative to the inner assembly/retrieval tool, according to the illustrated embodiment.

With further reference to FIG. 9A, a shaft subassembly of the retrieval tool/inner assembly of catheter 900 includes an elongate tubular sidewall 810, which may be secured to handle 950, so that shaft 910 may be moved relative thereto by control member 953. A capture member 830 of the retrieval tool/inner assembly is shown mounted to a flared distal end 812 of tubular sidewall 810, wherein both are contained in receptacle 930. According to the illustrated embodiment, receptacle 930 has a distal-most opening 903, which allows passage of implantable medical device 300 therethrough, and receptacle 930 is sized to contain device 300, along with capture member 830 and flared distal end 812 of tubular sidewall 810, for example, as shown in FIG. 10B.

Figure 9B:
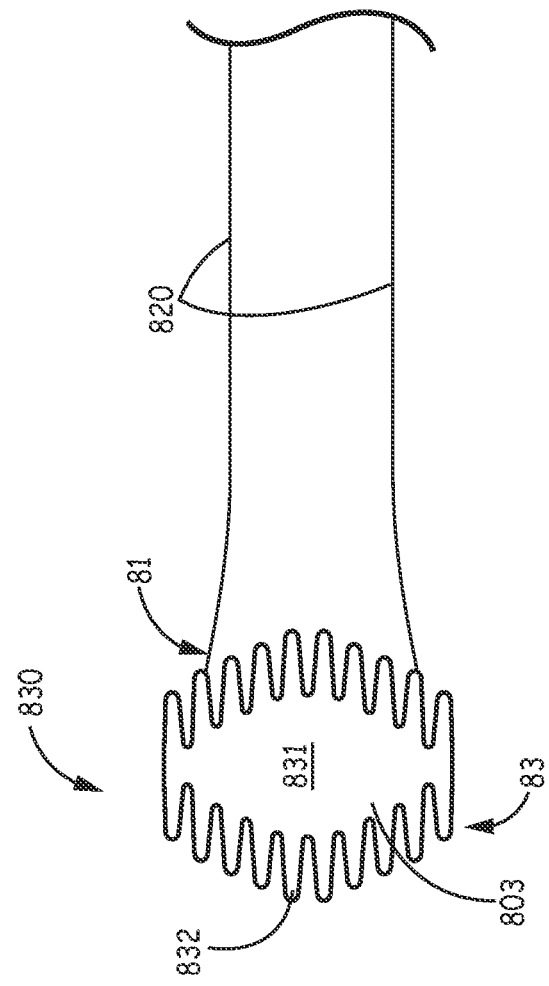
FIG. 9B is a perspective view of a capture member and associated tethers of the system shown in FIG. 9A, according to some embodiments.

FIG. 9B is a perspective view of capture member 830 and an associated pair of tethers 820, according to some embodiments. FIGS. 9A-B illustrate spring-biased perimeter sidewall 832 of capture member 830 defining a passageway 831 and extending from a proximal end 81 thereof to a distal end 83 thereof, which defines a distal-most opening 803 of passageway 831. Spring-biased sidewall 832 is shown formed by a 'serpentined' wire loop, for example, a Nitinol wire that has a diameter of approximately 0.01 inch, and has been formed to undulate in a sinusoidal fashion around a generally circular perimeter. FIG. 9A further illustrates perimeter sidewall 832 of capture member 830 constrained within device receptacle 930 of catheter 900 so that distal-most opening 803 is at a collapsed diameter, but, when catheter shaft 910 is retracted relative to capture member 830 and tubular sidewall 810, for example, via control member 953 of handle 950, so that capture member 830 is exposed outside of receptacle 930, distal-most opening 803 of capture member passageway 631 expands to a spring-biased diameter that is greater than a diameter of distal-most opening 903 of device receptacle 930, for example, being at least 5% greater, or up to 25% greater in some embodiments. Capture member passageway 831, at both the spring-biased and collapsed diameters, is sized to contain at least attachment member 310 and housing proximal end 381 of device 300.

Figure 9C:
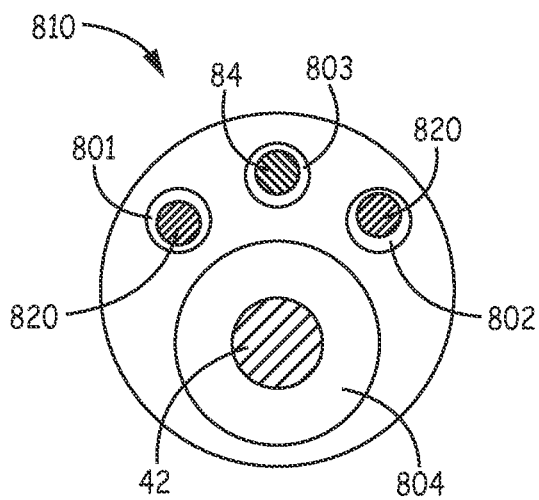
FIG. 9C is a cross-section view per section line C-C of FIG. 9A, according to some embodiments.
Figure 9D:
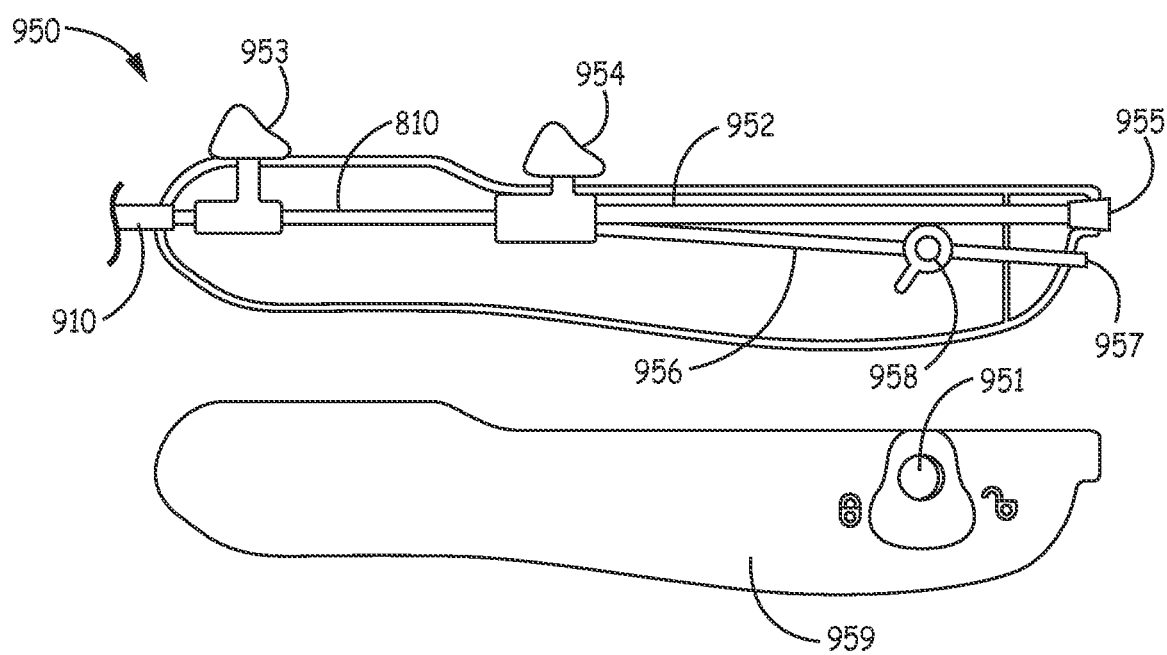
FIG. 9D is a plan view inside a handle of the system shown in FIG. 9A, according to some embodiments.

FIG. 9B further illustrates tethers 820 secured to capture member 830 and extending proximally therefrom, for example, to couple proximal end 81 of perimeter sidewall 832 to tubular sidewall 810 by extending within first and second lumens 801, 802 defined by tubular sidewall 810, as shown in FIG. 9C, which is a cross-section view per section line C-C of FIG. 9A, according to some embodiments. Tethers 820 may be polymer fibers tied to capture member 830 or metal wires/cables welded to capture member 830, according to methods known in the art. With reference to FIG. 9D, which is a plan view inside handle 950 of catheter 900, proximal ends of tethers 820 may extend within a tether conduit 956 within handle 950, and be secured therein by a clamping member 958, for example, a stop-cock valve, wherein the operator has access to clamping member 958 via an aperture 951 formed through a sidewall 959 of handle 950, to alternately secure and release tethers 820. (Sidewall 959 is removed from handle 950 to show the inside thereof.)

With further reference to FIG. 9A in conjunction with FIG. 9C, the retrieval tool/inner assembly of catheter 900 may include a steering subassembly, wherein an elongate pull wire 84 extends within a third lumen 803 of tubular sidewall 810 from a distal end thereof (not shown), which is coupled to a pull band 18 mounted to tubular sidewall 810 in proximity to flared distal end 812, to a proximal end thereof (not shown), which is coupled to an actuator 954 mounted to catheter handle 950. Catheter shaft 910, handle 950, and tubular sidewall 810 may be constructed in a manner similar to that for the tool described in the aforementioned and commonly assigned United States Patent Application US 2015/0094668, according to some embodiments. The retrieval tool/inner assembly of catheter 900 further includes snare member 42, similar to embodiments described above, wherein snare member 42 extends through a proximal port opening 955 and a snare conduit 952 of catheter handle 950, and within a fourth lumen 804 (FIG. 9C) defined by tubular sidewall 810, so that the operator can slide snare member 42 out through capture member passageway 831 (FIG. 9B), and open and close the loop of snare member 42 to snare implanted device 300, for example, as shown in FIG. 10A.

According to some embodiments, catheter 900 may initially be configured for deploying an implantable medical device, for example, device 300, wherein attachment feature 310 of device 300 is mounted to flared distal end 812 of inner assembly tubular sidewall 810, rather than capture member 830, and a tether that is joined to attachment feature 310 extends within lumens 801, 802 and tether conduit 956, rather than deployment member tethers 820. Thus, according to some methods, after deploying device 300 out through distal-most opening 903 of receptacle 930 to engage device fixation member 350 at the implant site, for example, according to methods described in the aforementioned '668 reference, the operator may reconfigure catheter 900 by removing the device tether from catheter 900, for example, by pulling the device tether out through a proximal opening 957 of tether conduit 956, and then assembling capture member 830 together with inner assembly tubular sidewall 810, as described above, and inserting snare member 42 through proximal port opening 955.

Figure 10A:
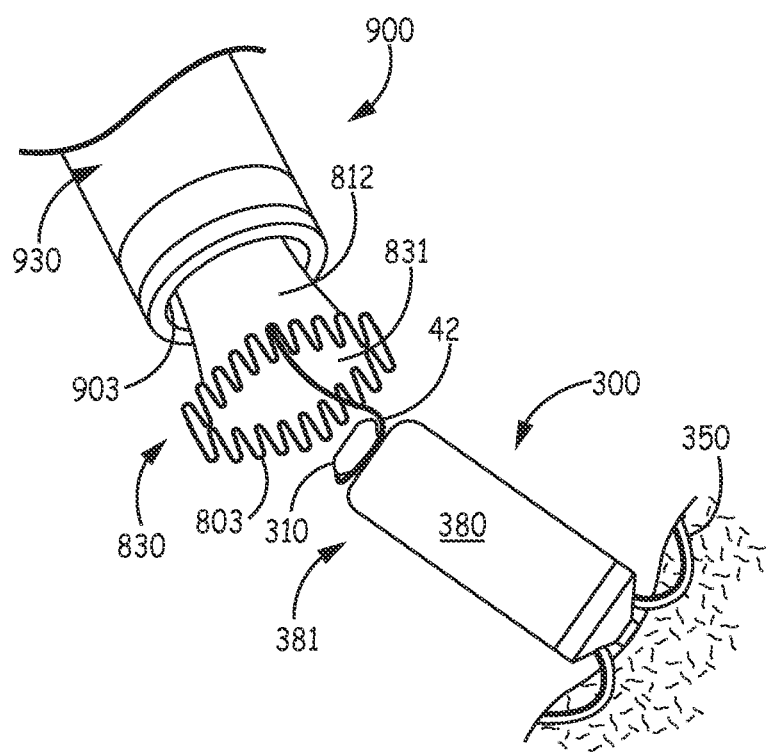
FIG. 10A is a schematic depicting the employment of the system of FIG. 9A, according to some methods.
Figure 10B:
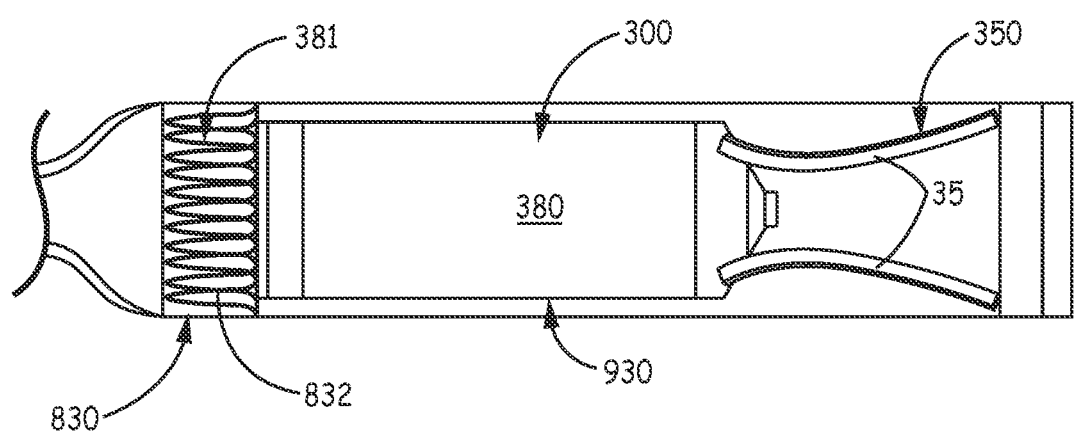
FIG. 10B is a longitudinal cross-section view of the system of FIG. 9A, according to some embodiments.

FIG. 10A is a schematic depicting an initial step in a method for retrieving implanted device 300 with catheter 900. FIG. 10A illustrates device receptacle 930 having been retracted to expose capture member 830 of the inner assembly/retrieval tool out through distal-most opening 903, wherein receptacle 930 of catheter 900 is positioned in proximity to an implant site, for example, near apex 103 of a right ventricle RV shown in FIG. 2, having been advanced through a 23 F introducer sheath that provides vascular access at a femoral vein puncture site (not shown). FIG. 10 further illustrates snare member 42 having been maneuvered to snare attachment feature 310 of device 300. With further reference to FIG. 8A, similar to the situations described above in conjunction with FIGS. 4B, 6A and 8A, the plane of receptacle distal-most opening 903 is misaligned with that of device proximal end 381. But, due to the expanded distal-most opening 803 of capture member passageway 831, at the spring-biased diameter, the operator can advance capture member 830 to 'funnel' attachment feature 310 and proximal end 381 of device housing 380 into capture member passageway 831, after which the operator can more easily advance receptacle 930 over the snared device 300. According to some methods, after advancing capture member 830 over attachment feature 310 and housing proximal end 381 of the snared device 300, the operator may advance device receptacle 930 over the snared device 300, for example, until distal-most opening 903 abuts the implant site, prior to applying a pull force to disengage device fixation member 350 from the implant site. FIG. 10B is a longitudinal cross-section view of receptacle 930 advanced over the snared device 300, after the operator has applied a pull force to disengage device fixation member 350 from the implant site.

FIG. 10B illustrates spring-biased perimeter sidewall 832 of capture member 830 surrounding proximal end 381 of device housing 380 within receptacle 930, and device receptacle 930 holding fingers 35 of device fixation member 350 in the extended condition.

In the foregoing detailed description, the invention has been described with reference to specific embodiments. However, it may be appreciated that various modifications and changes can be made without departing from the scope of the invention as set forth in the appended claims.

For example, the following Items are illustrative of further embodiments:

Item 1. An interventional medical system comprising an implantable medical device, a catheter, and a retrieval tool; the medical device comprising an electronic controller, a hermetically sealed housing containing the controller, an electrode electrically coupled to the controller and mounted in proximity to a distal end of the housing, an attachment feature joined to a proximal end of the housing, and a fixation member mounted to the distal end of the housing; the catheter comprising an elongate shaft and a device receptacle joined to a distal end of the shaft, the shaft including a longitudinally extending lumen, and the device receptacle being sized to contain the medical device therein and having a distal-most opening that allows passage of the medical device therethrough, and the device receptacle being in fluid communication with the shaft lumen; and the retrieval tool comprising an elongate snare member and a shaft assembly, the shaft assembly comprising an elongate tubular sidewall that defines a lumen configured to receive passage of the snare member therethrough, the elongate tubular sidewall configured for sliding engagement within the lumen of the catheter shaft; and wherein the shaft assembly of the retrieval tool further comprises:
a capture member comprising a collapsible spring-biased perimeter sidewall, the perimeter sidewall defining a passageway that is approximately coaxial, and in fluid communication with the lumen of the tubular sidewall of the retrieval tool shaft assembly, the perimeter sidewall extending from a proximal end thereof to a distal end thereof, the proximal end being coupled to the tubular sidewall of the shaft assembly, and the distal end defining a distal-most opening of the passageway; and
wherein the distal-most opening of the capture member passageway has a spring-biased diameter that is greater than a diameter of the distal-most opening of the device receptacle of the catheter;
the distal-most opening of the capture member passageway has a collapsed diameter that is less than the diameter of the device receptacle distal-most opening, when the capture member is received within the device receptacle; and
the capture member passageway is sized to contain the attachment member of the medical device and the proximal end of the medical device housing.

Item 2. The system of item 1, wherein:
the collapsible spring-biased perimeter sidewall of the capture member of the retrieval tool shaft assembly defines a flared outer surface of the capture member, when the distal-most opening of the passageway defined thereby is at the spring-biased diameter; and
a length of the capture member passageway is approximately equal to an overall length of the medical device.

Item 3. The system of any one of items 1-2, wherein the collapsible spring-biased perimeter sidewall comprises a flexible polymer mesh supported by a plurality of spring-biased ribs, a proximal end of each rib defining the proximal end of the perimeter sidewall, and the rib proximal ends being spaced apart from one another around a circumference of the tubular sidewall of the retrieval tool shaft assembly.

Item 4. The system of any one of items 1-3, wherein:
the spring-biased diameter of the distal-most opening of the capture member passageway of the retrieval tool shaft assembly is 2 to 5 times greater than the diameter of the distal-most opening of the device receptacle of the catheter; and
the collapsible spring-biased perimeter sidewall of the capture member comprises a flexible polymer mesh supported by a plurality of spring-biased ribs, a proximal end of each rib defining the proximal end of the perimeter sidewall, and the rib proximal ends being spaced apart from one another around a circumference of the tubular sidewall of the retrieval tool shaft assembly.

Item 5. The system of any one of items 1-4, further comprising:
a vacuum source adapted for coupling to the retrieval tool shaft assembly, so that suction can be applied through the lumen defined by the tubular sidewall and through the capture member passageway of the retrieval tool shaft assembly; and
wherein a length of the capture member passageway is approximately equal to an overall length of the medical device.

Item 6. The system of any one of items 1-5, wherein:
the tubular sidewall of the retrieval tool shaft assembly includes a flared distal end; and
the collapsible spring-biased perimeter sidewall of the capture member comprises a 'serpentined' wire loop mounted to the flared distal end of the shaft assembly tubular sidewall.

Item 7. The system of any one of items 1-6, wherein:
the retrieval tool shaft assembly further comprises a pair of elongate tethers extending along a length of the tubular sidewall thereof and on opposite sides of the lumen defined by the sidewall; and
the proximal end of the collapsible spring-biased perimeter sidewall is coupled to the shaft assembly tubular sidewall by the pair of elongate tethers.

Item 8. The system of any one of items 1-7, wherein the retrieval tool shaft assembly further comprises a steering subassembly; and wherein the steering subassembly comprises an elongate pull wire, a pull band, and an actuator, the pull wire extending along a length of the tubular sidewall of the shaft assembly from a proximal end of the wire to a distal end of the wire, the pull band being mounted to a distal end of the tubular sidewall of the shaft assembly, in proximity to the capture member, and being coupled to the distal end of the pull wire, and the actuator being mounted to a handle of the retrieval tool and being coupled to the proximal end of the pull wire.

Item 9. An assembly comprising a snare member and a shaft subassembly, the shaft subassembly comprising a tubular sidewall that defines a lumen configured to receive passage of the snare member therethrough, the tubular sidewall having a flared distal end defining a distal-most opening of the lumen, and the tubular sidewall being configured for sliding engagement within a catheter of an interventional medical system, the catheter including an elongate shaft and a device receptacle coupled to a distal end of the shaft, the device receptacle being in fluid communication with a lumen of the catheter shaft, and being sized to contain an implantable medical device therein, the device receptacle having a distal-most opening that allows passage of the medical device therethrough; and wherein the shaft subassembly of the assembly further comprises:
  a capture member comprising a collapsible spring-biased perimeter sidewall formed by a 'serpentined' wire loop mounted to the flared distal end of the tubular sidewall, the perimeter sidewall defining a passageway, the passageway being approximately coaxial, and in fluid communication with the lumen of the tubular sidewall; and
  wherein the passageway has a spring-biased diameter that is greater than a diameter of the device receptacle of the catheter, and has a collapsed diameter that is less than the diameter of the device receptacle, when the capture member is received within the device receptacle; and
  the capture member passageway is sized to contain a proximal end of a housing of the medical device and an attachment member of the medical device that is coupled to the proximal end of the housing.

Item 10. The assembly of item 9, wherein:
  the shaft subassembly further comprises a pair of elongate tethers extending along a length of the tubular sidewall thereof and on opposite sides of the lumen defined by the sidewall; and
  the collapsible spring-biased perimeter sidewall of the capture member is coupled to the tubular sidewall by the pair of elongate tethers.

Item 11. The assembly of any one of items 9-10, wherein the shaft subassembly further comprises a handle coupled to the proximal end of the tubular sidewall, the handle including a clamping member through which the pair of elongate tethers extend, the clamping member configured to alternately secure and release the tethers.

Item 12. A method for converting a catheter from a first configuration to a second configuration, the first configuration suitable for deploying an implantable medical device to an implant site, and the second configuration suitable for retrieving an implantable medical device from an implant site; and the method comprising:
  removing a device tether from first and second lumens of an inner assembly of the catheter, the first and second lumens being defined by a tubular sidewall of the inner assembly;
  mounting a capture member to a flared distal end of a tubular sidewall of the inner assembly by inserting a pair of capture member tethers into the first and second lumens, after removing the device tether therefrom, the flared distal end defining a distal-most opening for the first and second lumens and for a snare lumen defined by the tubular sidewall;
  collapsing a spring-biased sidewall of the mounted capture member within a device receptacle of the catheter, the device receptacle being coupled to a distal end of a shaft of an outer assembly of the catheter, the device receptacle being in fluid communication with a lumen of the shaft and having a distal-most opening that allows passage of a medical device therethrough, and the inner assembly being slideably engaged within the lumen of the outer assembly shaft; and
  inserting a snare member through the snare lumen of the inner assembly.

Item 13. The method of item 12, further comprising securing a proximal end of each of the capture member tethers within a clamping member of a handle of the catheter, after mounting the capture member to the inner assembly, the handle being coupled to a proximal end of the inner assembly tubular sidewall and to the outer assembly shaft.

Item 14. A method for retrieving an implantable medical device from an implant site, the medical device comprising an electronic controller, a hermetically sealed housing containing the controller, an electrode electrically coupled to the controller and mounted in proximity to a distal end of the housing, an attachment feature joined to a proximal end of the housing, and a fixation member mounted to the distal end of the housing, the fixation member comprising a plurality of fingers spaced apart from one another around a perimeter of the distal end of the housing, each finger being elastically deformable between a relaxed condition and an extended condition, a free end of each finger extending distally away from the distal end of the device housing, when the finger is in the extended condition, and the method comprising:
  advancing a device receptacle of a catheter of an interventional medical system to the implant site so that a distal-most opening of the device receptacle is located in proximity to the medical device, the device receptacle being coupled to a distal end of a shaft of the catheter, the device receptacle being in fluid communication with a lumen of the shaft and having a distal-most opening that allows passage of the medical device therethrough;
  snaring the attachment feature of the medical device with a snare member of a retrieval tool, the retrieval tool being in sliding engagement within the lumen of the catheter shaft, and the snare member being in sliding engagement within a lumen of a shaft assembly of the tool;
  causing a spring-biased sidewall of a capture member of the retrieval tool shaft assembly to open to a spring-biased diameter, the spring-biased sidewall defining a passageway in fluid communication and approximately coaxial with the lumen of the shaft assembly of the tool;
  advancing the capture member of the retrieval tool shaft assembly, with the spring-biased sidewall opened to the spring-biased diameter, over the snared device attachment feature and the proximal end of the device housing;
  applying a pull force, after advancing the capture member over the snared device attachment feature and the proximal end of the device housing, to disengage the device fixation member from the implant site; and
  advancing the device receptacle over the advanced capture member and the disengaged device to contain the capture member and the device in the receptacle so that the fingers of the device fixation member are held in the extended condition by the receptacle.

Item 15. The method of item 14, further comprising advancing the device receptacle of the catheter over the snared device with the capture member advanced thereover, prior to applying the pull force.

Item 16. The method of any one of items 14-15, wherein the device receptacle of the catheter is advanced over the snared device until the distal-most opening thereof abuts the implant site.

Item 17. The method of any one of items 14-16, further comprising deflecting the shaft assembly of the retrieval tool after snaring the device attachment feature and prior to advancing the device receptacle of the catheter over the snared device.

Item 18. The method of any one of items 14-17, wherein the capture member of the retrieval tool is advanced over the snared device until a distal end of the spring-biased sidewall thereof abuts the implant site; and further comprising applying a suction force through the lumen of the retrieval tool shaft assembly while applying the pull force.

Item 19. An interventional medical system comprising an implantable medical device, a device retrieval tool, and a catheter; the medical device comprising an electronic controller, a hermetically sealed housing containing the controller, an electrode electrically coupled to the controller and mounted in proximity to a distal end of the housing, an attachment feature joined to a proximal end of the housing, and a fixation member mounted to the distal end of the housing, the fixation member comprising a plurality of fingers spaced apart from one another around a perimeter of the distal end of the housing, each finger being elastically deformable between a relaxed condition and an extended condition, a free end of each finger extending distally away from the distal end of the device housing, when the finger is in the extended condition; the device retrieval tool configured to snare the attachment feature of the medical device; and the catheter comprising an elongate shaft and tubular sidewall that defines a device receptacle, the tubular sidewall being joined to a distal end of the shaft, the shaft including a longitudinally extending lumen configured to receive passage of the device retrieval tool therethrough, the device receptacle being in fluid communication with the shaft lumen, the receptacle having a length and a diameter uniform along the length, to hold the fingers of the device fixation member in the extended condition when the medical device is contained therein; and wherein an improvement to the tubular sidewall of the catheter comprises:

a flared inner surface defining a distal-most opening into the receptacle, the opening having a first diameter and a second diameter, the first diameter being equal to the diameter of the receptacle and the second diameter being at least 5% greater than the diameter of the receptacle, the second diameter being coincident with a distal-most edge of the tubular sidewall; and wherein a length of the flared inner surface is between 0.003 inch and 0.005 inch.

Item 20. The system of item 19, wherein the improvement further comprises a radiopaque filler blended into the tubular sidewall along the length of the flared inner surface.

We claim:

1. An interventional medical system comprising:
   an implantable medical device that includes an electronic controller, a hermetically sealed housing containing the controller, an electrode electrically coupled to the controller and mounted in proximity to a distal end of the housing, an attachment feature joined to a proximal end of the housing, and a fixation member mounted to the distal end of the housing;
   a catheter that includes an elongate shaft and a device receptacle joined to a distal end of the shaft, the shaft including a longitudinally extending lumen, and the device receptacle being sized to contain the medical device therein and having a distal-most opening that allows passage of the medical device therethrough, and the device receptacle being in fluid communication with the shaft lumen; and
   a retrieval tool that includes an elongate snare member and a shaft assembly, the shaft assembly comprising an elongate tubular sidewall that defines a lumen configured to receive passage of the snare member therethrough, the elongate tubular sidewall configured for sliding engagement within the lumen of the catheter shaft, and wherein the shaft assembly of the retrieval tool further comprises:
      a capture member comprising a collapsible spring-biased perimeter sidewall, the perimeter sidewall defining a passageway that is approximately coaxial and in fluid communication with the lumen of the tubular sidewall of the retrieval tool shaft assembly, the perimeter sidewall extending from a proximal end thereof to a distal end thereof, the proximal end being coupled to the tubular sidewall of the shaft assembly, and the distal end defining a distal-most opening of the passageway;
      wherein the distal-most opening of the capture member passageway has a spring-biased diameter that is greater than a diameter of the distal-most opening of the device receptacle of the catheter;
      the distal-most opening of the capture member passageway has a collapsed diameter that is less than the diameter of the device receptacle distal-most opening when the capture member is received within the device receptacle; and
      the capture member passageway is sized to contain the attachment member of the medical device and the proximal end of the medical device housing.

2. The system of claim 1, wherein:
   the collapsible spring-biased perimeter sidewall of the capture member of the retrieval tool shaft assembly defines a flared outer surface of the capture member, when the distal-most opening of the passageway defined thereby is at the spring-biased diameter; and
   a length of the capture member passageway is approximately equal to an overall length of the medical device.

3. The system of claim 2, wherein the collapsible spring-biased perimeter sidewall comprises a flexible polymer mesh supported by a plurality of spring-biased ribs, a proximal end of each rib defining the proximal end of the perimeter sidewall, and the rib proximal ends being spaced apart from one another around a circumference of the tubular sidewall of the retrieval tool shaft assembly.

4. The system of claim 1, wherein:
   the spring-biased diameter of the distal-most opening of the capture member passageway of the retrieval tool shaft assembly is 2 to 5 times greater than the diameter of the distal-most opening of the device receptacle of the catheter; and
   the collapsible spring-biased perimeter sidewall of the capture member comprises a flexible polymer mesh supported by a plurality of spring-biased ribs, a proximal end of each rib defining the proximal end of the perimeter sidewall, and the rib proximal ends being spaced apart from one another around a circumference of the tubular sidewall of the retrieval tool shaft assembly.

5. The system of claim 4, further comprising:
a vacuum source adapted for coupling to the retrieval tool shaft assembly, so that suction can be applied through the lumen defined by the tubular sidewall and through the capture member passageway of the retrieval tool shaft assembly; and
wherein a length of the capture member passageway is approximately equal to an overall length of the medical device.

6. The system of claim 1, wherein the retrieval tool shaft assembly further comprises a steering subassembly; and wherein the steering subassembly comprises an elongate pull wire, a pull band, and an actuator, the pull wire extending along a length of the tubular sidewall of the shaft assembly from a proximal end of the wire to a distal end of the wire, the pull band being mounted to a distal end of the tubular sidewall of the shaft assembly, in proximity to the capture member, and being coupled to the distal end of the pull wire, and the actuator being mounted to a handle of the retrieval tool and being coupled to the proximal end of the pull wire.

7. The system of claim 6, wherein the pull band is configured to deflect the shaft assembly to align the passageway of the perimeter sidewall with the attachment feature when the attachment feature is not aligned with the device receptacle.

8. The system of claim 7, wherein:
the steering assembly is a first steering assembly;
the pull wire is a first pull wire;
the pull band is a first pull band;
the actuator is a first actuator; and
the catheter further comprises a second steering assembly that comprises:
a second elongate pull wire that extends along the shaft of the catheter from a proximal end of the second pull wire to a distal end of the second pull wire;
a second pull band mounted in proximity to the distal end of the shaft of the catheter and coupled to the distal end of the second pull wire; and
a second actuator mounted to a handle of the catheter and being coupled to the proximal end of the second pull wire, wherein the second steering assembly is configured to deflect the distal end of the shaft when the second actuator is moved.

* * * * *